United States Patent [19]

Doersen et al.

[11] Patent Number: 5,286,644
[45] Date of Patent: Feb. 15, 1994

[54] RAT OSTEOSARCOMA CELL LINE OSR-2

[75] Inventors: Claus-Jens W. Doersen; Robert J. Isfort, both of Cincinnati, Ohio

[73] Assignee: The Procter & Gamble Company, Cincinnati, Ohio

[21] Appl. No.: 903,432

[22] Filed: Jun. 24, 1992

[51] Int. Cl.$^5$ .................. C12N 05/06; C12P 21/02
[52] U.S. Cl. .................. 435/240.2; 435/70.1; 435/240.1; 530/350
[58] Field of Search .............. 435/240.2, 240.1, 70.1; 530/350

[56] References Cited

U.S. PATENT DOCUMENTS

5,035,901  7/1991  Anderson et al. .................. 424/573

FOREIGN PATENT DOCUMENTS

0350641   1/1990   European Pat. Off. ..... A61K 37/02
WO91/18620 12/1991 PCT Int'l Appl. ......... A61K 37/02
WO91/18622 12/1991 PCT Int'l Appl. ......... A61K 37/36
2164042   3/1986   United Kingdom ........ A61K 37/00

OTHER PUBLICATIONS

Amitani, K., K. Ono, Y. Sakamoto and Y. Nakata., "Osteogenic Induction by Cell-free Material From Murine Osteosarcoma and its Cultured Cell Line", Gann, (Jun. 1975), vol. 66, No. 3, pp. 327-329.

Chandar, N., B. Billig, J. McMaster and J. Novak, "Inactivation of p53 Gene in Human and Murine Osteosarcoma Cells", British Journal of Cancer, (Feb. 1992), vol. 65, No. 2, pp. 208-214.

Huang, H. J. S., J. K. Yee, J. Y. Shew, P. L. Chen, R. Bookstein, T. Friedmann, E. Y. H. P. Lee and W. H. Lee, "Suppression of the Neoplastic Phenotype by Replacement of the RB Gene in Human Cancer Cells", Science, (Dec. 1988), vol. 242, pp. 1563-1566.

Ikeda, S., S. Hiroshi, K. Akiyama, S. Watanabe, S. Ito, H. Inoue, H. Takechi, G. Tanabe and T. Oda, "Amplification of Both c-myc and c-raf-1 Oncogenes in a Human Osteosarcoma", Jpn. J. Cancer Res., (1989), vol. 80, pp. 6-9.

Masuda, H., C. Miller, H. P. Koeffler, H. Battifora and M. J. Cline, "Rearrangement of the p53 Gene in Human Osteogenic Sarcomas", Proc. Natl. Acad. Sci., (Nov. 1987), vol. 84, pp. 7716-7719.

Majeska, R. J., S. B. Rodan and G. A. Rodan, "Parathyroid Hormone-Responsive Clonal Cell Lines from Rat Osteosarcoma", Endocrinology, (Nov. 1980), vol. 107, pp. 1494-1503.

Miller, C. W., A. Aslo, C. Tsay, D. Siamon, K. Ishizaki, J. Toguchida, T. Yamamuo, B. Lampkin and H. P. Koeffler, "Frequency and Structure of p53 Rearrangements in Human Osteosarcoma", Cancer Research, (Dec. 1990), vol. 50, pp. 7950-7954.

Rodan, G. A. and M. Noda, "Gene Expression in Osteoblastic Cells", Critical Review Eukaryotic Gene. Expression, (1991), vol. 1, Issue 2, pp. 85-91.

Rodan, G. A., J. K. Heath, K. Yoon, M. Noda and S. B. Rodan, "Diversity of the Osteoblastic Phenotype", Cell and Molecular Biology of Verterbrate Hard Tissues, (1988), Ciba Foundation Symposium 136, pp. 78-91.

(List continued on next page.)

Primary Examiner—Robert J. Hill, Jr.
Assistant Examiner—Sally P. Teng
Attorney, Agent, or Firm—Brahm J. Corstanje; Milton B. Graff IV; David L. Suter

[57] ABSTRACT

The present invention relates to a novel cell line isolated from a rat osteosarcoma having the following characteristics: a) a normal p53 gene as compared to a non-tumorigenic Sprague-Dawley rat cell control; b) a normal RB-1 gene as compared to a non-tumorigenic Sprague-Dawley rat cell control; c) a normal c-myc gene as compared to a non-tumorigenic Sprague-Dawley rat cell control; d) a normal c-fos gene as compared to a non-tumorigenic Sprague-Dawley rat cell control; e) a normal immediate early gene response following mitogenic stimulation; f) a canalicular Matrigel growth pattern; g) non-tumorigenic in congenitally athymic mice; h) high levels of alkaline phosphatase activity; i) a lack of autocrine growth factor production; and j) an ability to be serially propagated greater than sixty population doublings.

1 Claim, 2 Drawing Sheets

OTHER PUBLICATIONS

Sturm, S. A., P. G. Strauss, S. Adolph, H. Hameister and V. Erfle, "Amplification and Rearrangement of c-myc in Radiation-induced Murine Ossteosarcomas", Cancer Research, (Jul. 1990), vol. 50, pp. 4146–4153.

Wozney, J. M., V. Rosen, A. J. Celeste, L. M. Mitsock, M. J. Whitters, R. W. Kriz, R. M. Hewick and E. A. Wang, "Novel Regulators of Bone Formation: Molecular Clones and Activities", Science, (Dec. 1988), vol. 242, pp. 1528–1534.

Wrana, J. L., T. Kubota, Q. Zhang, C. M. Overall, J. E. Aubin, W. T. Butler and J. Sodek, "Regulation of Transformation-sensitive Secreted Phosphoprotein (SPP1/osteopontin) Expression by Transforming Growth Factor-$\beta$",.Biochem. J., (1991), vol. 273, pp. 523–531.

Vukicevic et al., 1990, Cell, vol. 63, pp. 437–445.

Smith H. S., 1979, J. Natl. Cancer Inst., vol. 62, pp. 225–230.

"Bone-inducing agent (BIA) from cultured human Saos-2 osteosarcoma cells", Anderson, H. C., K. Sugamoto, D. C. Morris, H. H. T. Hsu, & T. Hunt, Bone and Mineral, 16 (1992) pp. 49–62.

"Oncogene, Tumor Suppressor Gene, and Growth Signal Transduction Alterations in a Series of Chemically-Induced Rat Osteosarcomas", Isfort, R. J., D. C. Cody, G. Lovell, & C. J. Doersen, Poster Presentation, Seventh Annual Oncogene Meeting, Frederick, MD, Jun. 24, 1991.

"Growth Factors in Development, Transformation, and Tumorigenesis", Cross, M. and T. M. Dexter, Cell, vol. 64, pp. 271–280, (1991).

"Insulin Promotes Growth of the Cultured Rat Osteosarcoma Cell Line UMR-106-01:An Osteoblast-Like Cell", Hickman, J. and A. McElduff, Endocrinology, vol. 124, No. 2, pp. 701–706, (1989).

"Negative regulators of cell growth", Wang, J. L. and Y. M. Hsu, TIBS 11 (1986).

"Growth Factors: Mechanism of Action and Relation to Oncogenes", Heldin, C. H. and Westermark, B., Cell, vol. 37, pp. 9–20, (1984).

"Production of An Insulin-like Growth Factor by Osteosarcoma", Blatt, J., C. White, S. Dienes, H. Friedman and T. P. Foley, Jr., Biochemical and Biophysical Research Communications, vol. 123, No. 1, pp. 373–376, (1984).

RAT OSTEOSARCOMA CELL LINE OSR-2

TECHNICAL FIELD

This invention relates generally to a novel cell line, and specifically to a novel rat osteosarcoma cell line, as well as its use for screening for cell growth factors or cell differentiation factors.

BACKGROUND OF THE INVENTION

Polypeptide growth factors play a key role in regulating the development of multicellular organisms and in the processes of tissue maintenance and repair. (For recent reviews see Cross and Dexter (1991) *Cell*, Vol. 64, pp. 271-280; Aaronson (1991) *Science*, Vol. 254, pp. 1146-1153.) At the cellular level, growth factors are involved in regulating proliferation and the progressive acquisition of the differentiated phenotype. Growth factors are capable of stimulating cellular proliferation as well as inhibiting cellular proliferation and many growth factors have been found to be multifunctional (Sporn and Roberts (1988) *Nature*, Vol. 332, pp. 217-219). The highly coordinated functions of growth factors is perhaps best exemplified in the development of the hematopoietic cell system (Metcalf (1989) *Nature*, Vol. 339, pp. 27-30) where a limited number of stem cells give rise to a larger population of developmentally restricted progenitor cells. These progenitor cells are further stimulated to proliferate and differentiate into mature lymphoid, erythroid and myeloid cells.

Much of what we know about the functions of growth factors comes from in vitro studies using target cell lines that are capable of responding to growth factors in some measurable way. The ability of a particular target cell to respond to a growth factor is determined by the expression of a specific receptor which binds the factor and initiates a signal transduction cascade resulting in a cellular response. Furthermore, the nature of the response to a particular growth factor is often a function of the type of cell and the differentiated state of the cell. Thus, our ability to understand the function of known growth factors and to identify novel growth factors will be enhanced by expanding the repertoire of target cells representative of various cell lineages.

OBJECTS OF THE PRESENT INVENTION

It is an object of the present invention to provide a novel cell line suitable for screening for cell growth proteins.

It is also an object of the present invention to provide a method for screening for cell growth proteins including, but not limited to, growth factors and differentiation factors.

SUMMARY OF THE INVENTION

The present invention relates to a novel cell line isolated from a rat osteosarcoma having the following characteristics: a) a normal p53 gene as compared to a non-tumorigenic Sprague-Dawley rat cell control; b) a normal RB-1 gene as compared to a non-tumorigenic Sprague-Dawley rat cell control; c) a normal c-myc gene as compared to a non-tumorigenic Sprague-Dawley rat cell control; d) a normal c-fos gene as compared to a non-tumorigenic Sprague-Dawley rat cell control; e) a normal immediate early gene response following mitogenic stimulation; f) a canalicular Matrigel growth pattern; g) non-tumorigenic in congenitally athymic mice; h) high levels of alkaline phosphatase activity; i) a lack of autocrine growth factor production; and j) an ability to be serially propagated greater than sixty population doublings.

The present invention also relates to a method for screening for mitogenic growth factors comprising treating the novel rat osteosarcoma cell line with a protein of interest and measuring for an increase in growth activity of the treated cells as compared to untreated, control, cells.

The present invention also relates to a method for screening for differentiation factors comprising treating the novel rat osteosarcoma cell line with a protein of interest and measuring for a decrease in growth activity of the treated cells as compared to untreated, control, cells.

DETAILED DESCRIPTION OF THE INVENTION

As used herein, "growth factor" means a protein which plays a role in regulating the development of a cell. Such proteins include, but are not limited to, mitogenic growth factors and differentiation factors.

As used herein, "mitogenic growth factor" means a protein which induces a cell to grow and increase in number by means of reproduction of similar form.

As used herein, "differentiation factor" means a protein which induces a cell to specialize and acquire a character or function different from that of the original type.

As used herein, "target cell" and "treated cell" mean a cell treated by a protein of interest when screening for a cell growth protein.

As used herein, "untreated cell" means a cell not treated by a protein of interest (although such a cell may be subjected to other proteins) when screening for a cell growth protein. Such untreated cells are useful as controls when screening for a cell growth protein.

As used herein, "tumorigenic" means an ability to form a tumor in a host animal.

As used herein, "OSR-2" refers to the novel cell line of the present invention, American Type Culture Collection (ATCC) Accession No. CRL 11065.

As used herein, "w/v" and "v/v" refer to percent by weight and percent by volume, respectively.

The present invention relates to a novel cell line isolated from a rat osteosarcoma, the cell line having the following characteristics: a) a normal p53 gene as compared to a non-tumorigenic Sprague-Dawley rat cell control; b) a normal RB-1 gene as compared to a non-tumorigenic Sprague-Dawley rat cell control; c) a normal c-myc gene as compared to a non-tumorigenic Sprague-Dawley rat cell control; d) a normal c-fos gene as compared to a non-tunorigenic Sprague-Dawley rat cell control; e) a normal immediate early gene response following mitogenic stimulation; f) a canalicular Matrigel growth pattern; g) non-tumorigenic in congenitally athymic mice; h) high levels of alkaline phosphatase activity; i) a lack of autocrine growth factor production; and j) an ability to be serially propagated greater than sixty population doublings.

The present invention also relates to a method for screening for mitogenic growth factors comprising treating the novel rat osteosarcoma cell line with a protein of interest and measuring for an increase in growth activity of treated cells as compared to untreated, control, cells.

The present invention also relates to a method for screening for differentiation factors comprising treating the novel rat osteosarcoma cell line with a protein of interest and measuring for a decrease in growth activity of the treated cells as compared to untreated, control, cells.

Preferably such methods further comprise a) cultivating the novel cell line in growth medium, b) removing the growth medium form the cell line, c) cultivating the cell line in medium not containing a cell growth protein, d) exposing the cell line to a radioactive tracer, and e) assaying the radioactivity of the cell line.

The cell line of the present invention is useful for studying the role of known and potentially novel growth factors in the regulation of cells of osteoblast lineage.

Statement of Deposit

OSR-2 has been deposited at The American Type Culture Collection, 12301 Parklawn Drive, Rockville, Md. 20852, U.S.A., on Jun. 5, 1992. The deposited strain has been assigned Accession No. CRL 11065.

The subject cultures have been deposited under conditions that assure access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that Applicants' granting of permission to the depository to distribute samples of the deposit does not constitute an express or implied license to practice the invention claimed in any patent issuing on the subject application or any other patent.

The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

Isolation of the OSR-2 Cell Line

The OSR-2 cell line was established from a tumor excised from a Sprague-Dawley rat with multifocal metastatic osteosarcoma. The site of the excised tissue was the scapula. The tumor tissue was aseptically remove from the euthanized animal and carefully trimmed of connective tissues. The tumor was minced in a culture dish (100 mm diameter) containing 15 ml of growth medium (10% fetal bovine serum, 90% RPMI 1640 medium (GIBCO)) further supplemented with penicillin (100 units/ml, GIBCO), Fungizone (0.25 microgram/ml, GIBCO) and streptomycin (100 micrograms/ml,GIBCO), and incubated at 37° C. in an atmosphere of 5% $CO_2$ and 95% air with a relative humidity of approximately 95%. The adherent cells which migrated from the minced tumor pieces onto the surface of the culture dish were further expanded as a cell population using standard tissue culture techniques. Once the OSR-2 cell line reached confluence in a tissue culture flask (150 $cm^2$ surface area), the cell line was designated as having a mean population doubling of 1. At this stage, the cells were subcultured in growth medium (10% fetal bovine serum, 90% RPMI 1640 medium) with no antibiotic or antimycotic supplements. The OSR-2 cell line was routinely tested for mycoplasma contamination by DAPI assay (Stanbridge (1981) *Isr. J. Med. Sci,* Vol. 17, pp. 563–568) and was found to be negative.

Characteristics of the OSR-2 Cell Line

The OSR-2 cell line can be serially propagated in culture with no known limited life span. Cell cultures with a mean population doubling ranging from 56 to 70 are routinely used as target cells for assaying the mitogenic effects of growth factors. Although the OSR-2 cell line appears to have an indefinite life span in culture, the cells remain non-tumorigenic when assayed in congenitally athymic (nu/nu) mice (Harlan Laboratories). The subcutaneous injection of $1 \times 10^7$ cells per site into the midflank region of athymic mice does not result in tumor formation in any of the 16 sites (8 animals) observed for at least 12 months.

The OSR-2 cell line displays an osteoblast-like phenotype in vitro. The cells show positive staining for the presence of alkaline phosphatase (Rodan and Rodan (1983) *Bone and Mineral Research,* Annual 2 (Peck, ed.) pp. 244–285) as detected by a cytochemical assay (Sigma Chemical Company, Procedure 85). It has been reported (Vukicevic et al., (1990) *Cell,* Vol. 63, pp. 437–445) that osteoblastic cells are capable of forming cell clusters exhibiting networks of canalicular cell processes when cultured on reconstituted basement membrane extracts such as Matrigel (Collaborative Biomedical Products). Fibroblasts, chondrocytes and embryonic stem cells did not demonstrate the canalicular cell processes. OSR-2 cells when cultured on Matrigel at a density of approximately 50,000 cells per well of a standard 24-well tissue culture plate demonstrated the characteristic canalicular network that was very similar in appearance to the network formed by the osteoblastic MC3T3-E1 cells plated at an equivalent density (Sudo et al., (1983) *J. Cell Biol.,* Vol. 96, pp. 191–198; Vukicevic et al., (1990) *Cell,* Vol. 63, pp. 437–445).

Molecular Characterization of the OSR-2 Cell Line

In order to characterize the OSR-2 cell line in terms of unique mutations which can identify this cell line we have screened the cell line for mutations in genes which are commonly mutated in osteosarcomas. This molecular fingerprint of the OSR-2 cell provides a convenient and useful way to identify this cell line because these mutations are critical for the growth of these cells and is not expected to change.

In this respect human osteosarcomas have been extensively studied with respect to mutations in the retinoblastoma (RB-1) and p53 tumor suppressor genes (Iavarone et al., (1992) *Proc. Natl. Acad. Sci. USA,* Vol. 89, pp. 4207–4209; Diller et al., (1990) *Mol. Cell. Biol.*, Vol. 10, pp. 5772–5781; Masuda et al., (1987) *Proc. Natl. USA*, Vol. 84, pp. 7716–7719; Levine and Momand (1990) *Biochem. et Byophys. Acta*, Vol. 1032, pp. 119–136; Miller et al., (1990) *Cancer Res.*, Vol. 50, pp. 7950–7954; Friend et al., (1987) *Proc. Natl Acad. Sci. USA*, Vol. 84, pp. 9059–9063; Mulligan et al., (1990) *Proc. Natl Acad. Sci. USA*, Vol. 87, pp. 5863–5867; Hansen et al., (1985) *Proc. Natl. Acad. Sci. USA*, Vol. 82, pp. 6216–6220; Horowitz et al., (1989) *Science*, Vol. 243, pp. 937–940; Toguchida et al., (1989) *Nature*, Vol. 338, pp. 156–158). RB-1 mutations include point mutations, deletions, and splicing mutations (Friend et al., (1987) *Proc. Natl. Acad. Sci. USA*, Vol. 84, pp. 9059–9063; Levine and Momand, (1990) *Biochem. et Biophys. Acta*, Vol. 1032, pp. 119–136; Mori et al., (1990) *Oncogene*, Vol. 5, pp. 1713–1717; Horowitz et al., (1989) *Science*, Vol. 243, pp. 937–940). All of these mutations result in the production of a non-functional RB-1 protein. RB-1 is believed to function by acting as a "brake" on cellular proliferation at the appropriate time in the cell cycle. Control of the RB-1 function is achieved by selective and timely phosphorylation of RB-1 protein; phosphorylated RB-1 allows cellular proliferation while unphosphorylated RB-1 protein inhibits cellular proliferation (Laiho et al., (1990) *Cell*, Vol. 62, pp. 175–185; DeCaprio et al., (1989) *Cell*, Vol. 58, pp. 1085–1095; Buchkovich et al., (1989) *Cell*, Vol. 58, pp. 1097–1105; Chen et al., (1989) *Cell*, Vol. 58, pp. 1193–1198; Furukawa et al., (1990) *Proc. Natl Acad. Sci. USA*, Vol. 87, pp. 2770–2774). RB-1 control of cellular proliferation is one part of a closely regulated network of cell cycle controls, which include the cell cycle control proteins c-myc, c-fos and TGF-B (Laiho et al., (1990) *Cell*, Vol. 62, pp. 175–185; Moses et al., (1990) *Cell*, Vol. 63, pp. 245–247; Robbins et al., (1990) *Nature*, Vol. 346, pp. 668–671).

The p53 tumor suppressor gene was originally identified as an SV40 large T antigen binding protein whose expression was greatly increased (approximately 5–100 fold at the protein level) during SV40 cellular transformation (Levine and Momand, (1990) *Biochem. et Biophys. Acta*, Vol. 1032, pp. 119–136; Levine et al., (1991) *Nature*, Vol. 351, pp. 453–456). The p53 gene has since been found to be mutated in a variety of tumor types (Hollstein et al., (1991) *Science*, Vol. 253, pp. 49–53) including human osteosarcoma cells (Mulligan et al., (1990) *Proc. Natl. Acad. Sci. USA*, Vol. 87, pp. 5863–5867; Miller et al., (1990) *Cancer Res.*, Vol. 50, pp. 7950–7954; Masuda et al., (1987) *Proc. Natl Acad. Sci. USA*, Vol. 84, pp. 7716–7719; Diller et al., (1990) *Mol. Cell. Biol.*, Vol. 10, pp. 5772–5781). Mutation of the p53 gene either results in an altered protein which does not function normally or a complete loss of protein. Both of these mechanisms result in the absence of a functional p53 protein (Halevy et al., (1990) *Science*, Vol. 250, pp. 113–116; Chen et al., (1990) *Science*, Vol. 250, pp. 1576–1580; Milner and Medcalf, (1991) *Cell*, Vol. 65, pp. 765–774) and cellular transformation. The p53 protein is believed to function in several ways. The p53 protein is a transcriptional activator since p53 protein binds to specific DNA sequences (Raycroft et al., (1990) *Science*, Vol. 249, pp. 1049–1051; Kern et al., (1991) *Science*, Vol. 252, pp. 1708–1711) and contains an $NH_2$-terminal acidic domain which efficiently activates the transcription of genes in both yeast and mammalian cells (Fields and Jang, (1990) *Science*, Vol. 249, pp. 1046–1049). The protein produced from mutated p53 genes does not transcriptionally activate responsive genes (Raycroft et al., (1990) *Science*, Vol. 249, pp. 1049–1051). In addition, p53 regulates DNA replication since wild-type protein but not protein from mutated p53 genes associates with replication acomplexes (Levine et al., (1991) *Nature*, Vol. 351, pp. 453–456; Levine and Momand, (1990) *Biochem. et Biophys. Acta*, Vol. 1032, pp. 119–136) and is phosphorylated by p34(cdc2)-p60 and p34(cdc2)-cyclin B complexes (Bischoff et al., (1990) *Proc. Nat. Acad. Sci. USA*, Vol. 87, pp. 4766–4770; Milner et al., (1990) *EMBO J*, Vol. 9, pp. 2885–2889).

Two additional transforming genes which have been implicated in human and non-human osteosarcoma formations are the c-fos and c-myc oncogenes. The oncogenic variant of c-fos, v-fos, was first isolated as the transforming gene in retroviruses which resulted in murine osteosarcoma formation (Varmus (1984) *Ann. Rev. Genet.*, Vol. 18, pp. 553–612). Interestingly, transgenic mice carrying the v-fos oncogene display both cartilage and osteosarcoma tumors (Wang et al., (1991) *EMBO J*, Vol. 10, pp. 2437–2450). Oncogenic mutation of c-fos results when the fos gene is either over expressed or inappropriately expressed as a result of either viral transduction or mutation. C-fos functions in the cell, in conjunction with c-jun, as the complex which binds the AP-1 transcriptional activation site (Abate et al., (1990) *Science*, Vol. 249, pp. 1157–1161; Sassone-Corsi et al., (1988) *Cold Spring Harbor Symposia on Quantative Biology* LIII, 749–760).

C-myc has been found to be mutated both in radiation induced murine osteosarcomas (Sturm et al., (1990) *Cancer Res.*, Vol. 50, pp. 4146–4153) and in primary human osteosarcoma tumors (Bogenmann et al., (1987) *Cancer Res.*, Vol. 47, pp. 3808–3814). The myc oncogene was originally identified as the transforming gene in several retroviruses (v-myc) and c-myc mutations in a variety of tumor types were later identified (DePinho et al., (1987) *J. Cell Biochem.*, Vol. 33, pp. 257–266; Varmus (1984) *Ann. Rev. Genet*, Vol. 18, pp. 553–612). C-myc is most commonly amplified or translocated, both of which, along with retroviral transduction, result in the inappropriate expression of the myc gene (Varmus (1984) *Ann. Rev. Genet.*, Vol. 18, pp. 553–612; DePinho et al., (1987) *J. Cell Biochem*, Vol. 33, pp. 257–266). Myc protein and the Max protein form a complex which binds the regulatory region of genes, via a unique sequence, to control their expression (Blackwood and Eisenman, (1991) *Science*, Vol. 251, pp. 1211–1217; *Cole* (1991), Vol. 65, pp. 715–716). C-myc, along with c-fos are immediate early genes and are believed to play a central role in mitogenic signalling in the cell (Rozengurt (1986) *Science*, Vol. 234, pp. 161–166).

An additional way to assay c-fos and c-myc functional activity is to determine if these genes are transcriptionally activated following mitogenic stimulation. C-fos and c-myc are both members of a class of genes called the immediate early genes(Sassone-Corsi et al., (1988) *Cold Spring Harbor Symposia on Quantitative Biology* LIII, 749–760; Depinho et al., (1987) *J. Cell Biochem.*, Vol. 33, pp. 257–266). Genes in this class are transcriptionally activated following mitogenic stimuli usually within 1 hour and without the need of protein synthesis (Almendral et al., (1988) *Mol. Cell. Biol.*, Vol. 8, pp. 2140–2148; Greenberg et al., (1986) *Mol. Cell. Biol.*, Vol. 6, pp. 1050–1057). Since this is a complex pathway, alterations in immediate early gene transcription is indicative of either a mutation in the cellular pathway which leads from the receptor/plasma membrane to the gene/nucleus of the cell or a mutation which leads to the autocrine expression of a growth factor. Either of the above mutated phenotypes lead to a down regulation and subsequent inhibition of expression of the c-myc and c-fos genes following serum starvation and mitogen stimulation.

Characterization of Tumor Suppressor Genes and Oncogenes

High molecular weight DNA was isolated from the OSR-2 cell line as follows. Approximately $1 \times 10^8$ cells were cultured as described above until confluent. These cells were then scraped off the tissue culture flask into culture media, collected by centrifugation at 3300 g for 5 minutes, the culture media was removed from the cell pellet and the pellet was resuspended in 9.5 ml of NET buffer (100 mM sodium chloride, 10 mM Tris - pH 8.0, 1 mM EDTA). To the resuspended DNA was added 50 ul of 10 mg/ml of proteinase K (Boehringer Mannheim) and 0.5 ml of 10% (w/v) sodium dodecyl sulphate/water. This mixture was mixed well and incubated at 55° C. for one hour followed by extraction twice with an equal volume of a 50:50 mixture of phenol:chloroform. The aqueous phase was collected by centrifugation at 3300 g for 5 minutes and re-extracted with an equal volume of chloroform. The aqueous phase was collected by centrifugation at 3300 g for 5 minutes, removed to a new tube and to it was added 1 ml of 3M sodium acetate pH 5.2 and 20 ml of 100% ethanol. This solution was mixed well and incubated at $-20°$ C. for 2 hours followed by the collection of high molecular weight DNA by centrifugation at 3300 g for 30 minutes. The high molecular weight DNA was washed once with 5 ml of 70% ethanol/water (v/v), dried and resuspended in TE (10 mM Tris-pH 8.0 and 1 mM EDTA) at a concentration of 1 mg/ml.

For restriction enzyme analysis, 20 ug of the above isolated high molecular weight DNA in 20 ul TE was added to 2.5 ul of $10\times$ restriction enzyme buffer ($1\times$ restriction enzyme buffer consist of 50 mM Tris - pH 8.0, 10 mM magnesium chloride, and 100 mM sodium chloride) and 2 ul of restriction enzyme (either Eco R1 or Hind III at 10 units/ml both from New England Biolabs) and this mixture was incubated at 37° C. for 16 hours. Following incubation, the above solution was added to 3 ul of $10\times$ gel loading buffer ($10\times$ gel loading buffer is 0.25% bromophenol blue, 0.25% xylene cyanol, 25% Ficoll type 400, 10 mM EDTA in water) and the restriction endonuclease generated fragments were separated by agarose gel electrophoresis. Agarose gel electrophoresis was performed as follows. A 0.6% (w/v) agarose (Bethesda Research Laboratories) gel in $1\times$ TBE ($1\times$ TBE consist of 0.089M Tris, 0.089M boric acid, and 0.002 M EDTA) was poured in a BioRad horizontal gel electrophoresis apparatus, the above DNA solution was loaded into a well and electrophoresis was performed in a $1\times$ TBE solution for 16 hours at 20 volts. Following electrophoresis, the gel was stained for 1 hour in 0.5 ug/ml ethidium bromide (Sigma Chemical Company)/water solution followed by photography under 302 nm ultraviolet light irradiation. The gel was then prepared for Southern blotting as follows. The gel was soaked for 1 hour in a solution of 1.5M sodium chloride and 0.5M sodium hydroxide with constant shaking followed by an incubation for 1 hour in a solution of 1.5M sodium chloride and 1M Tris - pH 8.0 with constant shaking. The gel was then transferred to an LKB VacuBlot apparatus (LKB Scientific) prefitted with a sheet of BAS-NC nitrocellulose (Schleiser and Schuel) and the transfer of DNA from the agarose gel to the nitrocellulose membrane was performed under 40 cm.$H_2O$ of pressure using $10\times$ SSC ($10\times$ SSC is 1.5M sodium chloride and 0.15M sodium citrate, pH 7.0) as the transfer medium. The OSR-2 DNA Southern blot was then used in a hybridization analysis as follows. The nitrocellulose filter was first wet in $6\times$ SSC followed by prehybridization in hybridization buffer (50% formamide (molecular biology grade, Bethesda Research Laboratories), $5\times$ Denhardt's solution (Denhardt's solution is 0.1% Ficoll, 0.1% polyvinylpyrrolidone, and 0.1% bovine serum albumin—pentax fraction V—all from Sigma Chemical Company)), $5\times$ SSPE ($20\times$ SSPE is 3M sodium chloride, 0.2M sodium phosphate, and 0.02M EDTA—pH 7.4), 0.1% sodium dodecyl sulphate, and 100 ug/ml of denatured salmon sperm DNA (Sigma Chemical Company) for 4 hours at 42° C. with constant agitation. Molecular probes for the tumor suppressor genes RB-1 (ATCC #57450) and p53 (Levine and Momand (1990) *Biochemical et Biophysical Acta*, Vol. 1032, pp. 119-136) and the oncogenes c-myc (ATCC #41008) and c-fos (ATCC #41040) were radiolabelled using an Amersham nick translation kit and [32P]dCTP (ICN) to a specific activity of $1 \times 10(8)$ cpm/ug DNA by following the manufacturer's recommendations. These radiolabelled probes were then added to the hybridization solution/nitrocellulose filter of the prehybridization step and incubated at 42° C. for 40 hours with constant agitation. Following hybridization, the nitrocellulose filters (blots) were first incubated in $2\times$ SSC and 0.1% SDS at room temperature for 1 hour followed by an incubation in $0.2\times$ SSC and 0.1% SDS at 65° C. for 1 hour. The results of the hybridization experiment were visualized by autoradiography at $-70°$ C. Following autoradiography, the films were photographically developed and used in data analysis. The molecular analysis of the OSR-2 cell line RB-1, p53, c-myc and c-fos genes indicated that all these genes appeared normal (non-mutated, wild-type) as compared to a non-tumorigenic Sprague-Dawley rat cell control.

RB-1 and p53 Protein Analysis

Immunological identification of the p53 and RB-1 proteins were performed as follows. $1 \times 10^6$ OSR-2 cells were labelled for 4 hours with 100 uCi/ml of [35S]methionine (TranSlabel - ICN) in methionine-free RPMI-1640 (GIBCO) media containing 10% fetal bovine serum for 4 hours at 37° C. Following labelling, the cells were scraped off the tissue culture plate into the labelling media, the cells were collected by centrifugation at 3300 g for 5 minutes, followed by removal of the labelling media and the snap freezing of the cell pellet in liquid nitrogen. The frozen cell pellets were dissolved in 1 ml of ice-cold lysis buffer (50 mM Tris - pH 8.0, 5 mM EDTA, 150 mM sodium chloride, 0.5% Nonidet P-40, and 1 mM phenylmethylsulfonylfluoride) by vigorous vortexing and incubated on ice with intermediate vortexing for 30 minutes. The lysates were clarified of nonsoluable material by centrifugation at 10,000 g for 30 minutes, the supernate was removed to a new tube to which was added 10 ul of antibodies specific for either mutant p53 (Oncogene Science p53 Ab-3), normal and mutant p53 (Oncogene Science p53 Ab-1), or RB-1 (a 50:50 mixture of Oncogene Science RB Ab-2 and Ab-3), and 50 ul of a Protein A/G agarose (Boehringer Mannheim):lysis buffer (50:50). The above mixture was incubated overnight at 4° C. with constant shaking. The cell lysate was aspirated off and the antigen/antibody/-protein A-G pellet was washed one time in 1 ml of lysis buffer, one time in 1 ml of SNTE buffer (50 mM Tris-pH 7.4, 5 mM EDTA, 5% sucrose - w/v, 1% Nonidet P-40, and 0.5M sodium chloride), and one time in 1 ml of RIPA buffer (50 mM Tris - pH 7.4, 150 mM sodium chloride, 1% Triton X-100, 0.1% sodium dodecyl sulphate and 1% sodium deoxycholate). Following washing, the antigen/antibody/protein A-G agarose pellet was redissolved in 25 ul of sample buffer (62.5 mM Tris - pH 6.8, 2% sodium dodecyl sulphate, 10% glycerol, 5% 2-mercaptoethanol), boiled at 100° C. for 2-3 minutes, and applied to a well of a 10% SDS-PAGE gel. SDS-PAGE was performed as described by Laemmli (Laemmli, U.K. (1970) *Nature*, Vol. 227, pp. 680-685) for 6-8 hours at 30 mA constant current per gel. Following electrophoresis, the SDS-PAGE gels were incubated in 30% methanol and 10% acetic acid for at least 1 hours, impregnated with ENHANCE (NEN-DuPont) according to the manufacturer's recommendations, dried onto Whatman 3 mm paper using a BioRad gel dryer set at 60° C. for 2 hours and autoradiography at −70° C. was performed.

The results of the p53 and RB-1 protein analysis of the OSR-2 cell line indicated that both p53 and RB-1 protein were normal both in their level of expression and the protein's physical characteristics.

Immediate Early Gene Expression Following Mitogen Stimulation

In order to characterize the immediate early gene (c-myc and c-fos) transcription following mitogen stimulation in the OSR-2 cell line, the following experiments were performed. Approximately $1 \times 10^8$ cells were grown to 70% confluence in a tissue culture flask in 25 ml of standard growth media. The cells were washed 2 times with serum-free media followed by the addition of 25 ml of serum-free culture media and incubated for 12-16 hours at 37° C. under an atmosphere of 10% carbon dioxide in an incubator. To the serum-starved cells was added 3 ml (10% v/v) of fetal bovine serum and 10 ug/ml of cycloheximide and the cells were incubated as above for 3 hours. One group of cells was not mitogen stimulated and remained serum-starved. RNA from the mitogen stimulated and non-stimulated cells was isolated using the RNAzol (Cinna-/Biotecx Inc.) methodology according to the manufacturer's recommendation. Briefly, $1 \times 10^8$ cells were lysed in situ with 10 ml of RNAzol, the lysate was collected, 1 ml of chloroform was added to the lysate, the samples were vortexed vigorously for 15 seconds, and the mixture was then centrifuged at 12,000 g (4° C.) for 15 minutes. The upper (aqueous) phase was transferred to a new tube, an equal volume of isopropanol was added to it, the samples were cooled to −20° C. for 45 minutes, followed by pelleting of the RNA by centrifugation at 12,000 g (4° C.) for 15 minutes. The pelleted RNA was washed once with ice-cold 70% ethanol/water, dried, and resuspended in RNAse-free water at 20 ug/4.5 ul. RNA formaldehyde agarose gel electrophoresis was performed as described (Sambrook et al., (1989) Molecular Cloning, Cold Spring Harbor Press, Cold Spring Harbor, N.Y.) Briefly, 20 ug of total cellular RNA was denatured by heating to 55° C. for 15 minutes in denaturation buffer (4.5 ul RNA solution, 2.0 ul 10× RNA gel buffer (0.2M MOPS - pH 7.0, 50 mM sodium acetate, and 10 mM EDTA), 3.5 ul formaldehyde and 10.0 ul formamide)) followed by the addition of 2 ul of loading buffer (50% glycerol, 1 mM EDTA, 0.4% bromophenol blue, and 0.4% xylene cyanol) and loading of the sample into a well of the formaldehyde gel (1% agarose, 20 Mm M -OPS - pH 7.0, 5 mM sodium acetate, 1 mM EDTA and 2.2M formaldehyde). Electrophoresis was performed at 30 volts (constant voltage) for 16 hours. Following electrophoresis the gel was stained with ethidium bromide (0.5 ug/ml in water) for 1 hour, destained in water for 1 hour, and photographed under 300 nm ultraviolet light using a Foto-/Prep I (Fotodyne) transilluminator. Following photography, the gel was transferred to nitrocellulose (Schleicher & Schuell, BA-S NC) using a LKB Vacugene vacublotting apparatus operating at 50 cm$^2$ H$_2$O pressure provided with a 20× SSC (3M sodium chloride and 0.3M sodium citrate - pH 7.0) fluid transfer medium. Following transfer, the RNA was fixed to the nitrocellulose filter by UV irradiation using a Stratalinker (Stratagene Inc.) UV crosslinker at 0.12 Joules/cm$^2$. Following RNA fixation, the Northern blots were used in probe hydridization studies following previously described procedures (Sambrook et al., (1989) Molecular Cloning, Cold Spring Harbor Press, Cold Spring Harbor, N.Y.) that were modified as follows. The probes of interest, c-fos (ATCC #41040) or c-myc (ATCC #41008) were radioactively labelled by using an Amersham nick translation kit following the manufacturer's recommendations. Briefly, 1 ug of probe DNA was incubated with 1× nick translation buffer, 50 uCi alpha [$^{32}$P]-dCTP (NEN), and polymerase mix in a total volume of 20 ul at 15° C. for 2 hours followed by the addition of 80 ul of 1× STE (100 mM sodium chloride, 10 mM Tris - pH 8.0, and 1 mM EDTA). Separation of the incorporated from non-incorporated nucleotides was achieved using a Biospin column (BioRad). Typically 1 ug of probe had a specific activity of greater than $1 \times 10^8$ dpm. Following nick translation, the probe was boiled for 10 minutes and added to a prehybridized filter (4 hours in hybridization solution at 42° C.) in 10 ml of hybridization solution [6× SSPE (3M sodium chloride, 0.2M sodium phosphate - pH 7.4 and 20 mM EDTA), 5× Denhardt's solution (1% Ficoll, 1% polyvinyl- pyrrolidone, and 1% BSA - Pentax fraction V), 0.5% sodium dodecyl sulfate, 100 ug/ml denatured - sonicated salmon sperm DNA, and 50% formamide-] and incubated for 48 hours at 42° C. Following hybridization the filters were washed at room temperature in 2× SSC - 0.1% SDS followed by a wash at 65° C. with 0.2X SSC - 0.1% SDS. The filters were then dried, mounted to 3MM paper (Whatman) and autoradiography at −80° C. was performed using intensifying screens (NEN).

The OSR-2 cell line displayed a normal immediate early gene response with an increase in both the c-fos and c-myc gene transcription following mitogen stimulation.

TABLE 1

Characterizations of the OSR-2 cell line

The OSR-2 cell line has the following characteristics;
a. a normal p53 gene/protein as compared to a non-tumorigenic Sprague-Dawley rat cell control
b. a normal RB-1 gene/protein as compared to a non-tumorigenic Sprague-Dawley rat cell control c. a normal c-myc as compared to a non-tumorigenic Sprague-Dawley rat cell control
d. a normal c-fos gene as compared to a non-tumorigenic Sprague-Dawley rat cell control
e. a normal immediate early gene response following mitogenic stimulation
f. a canalicular Matrigel growth pattern
g. non-tumorigenic in congenitally athymic mice
h. high levels of alkaline phosphatase activity
i. a lack of autocrine growth factor production
j. an ability to be serially propagated greater than sixty population doublings

Use of the OSR-2 Cell Line as an Indicator Cell for Mitogenic Growth Factors

The ability of a growth factor to stimulate, or inhibit DNA synthesis in a serum-starved quiescent cell is perhaps the most widely studied response to growth factors. This ability to stimulate, or inhibit the mitogenic response of a target cell is an indicator of the growth factor's ability to stimulate, or inhibit cellular proliferation. The mitogenic response of cells can be quantitated using a [$^3$H]thymidine incorporation assay as previously described (Isfort (1990) *Somatic Cell Molec. Genet.*, Vol. 16, pp. 109-121). Briefly, target cells are plated at $2 \times 10^3$ cells per well in a 96 well micro-titer plate and cultured overnight in growth medium to allow the cells to attach. The growth medium is removed and the cells are washed three times with phosphate buffered saline (GIBCO) followed by an 8 hour incubation in 50 ul/well of serum-free medium. Mitogens such as serum and various growth factors are added to the serum starved cells in a volume of 50 ul of medium, with serum-free medium serving as a control. After 16 hours incubation, the cells are exposed to 1$\mu$Ci [$^3$H]thymidine for 6 additional hours of incubation. The cells are then harvested and lysed on glass fiber filters using a PHD cell harvester (Cambridge Technology, Inc.) and the radioactivity in the samples was assayed by scintillation spectrophotometery.

OSR-2 cells were found to respond mitogenically to a variety of known growth factors. All growth factors were purchased from GIBCO BRL, Life Technologies, Inc., and were tested over a 3-4 log concentration range incorporating the effective concentrations suggested by the supplier. The growth factors eliciting a positive mitogenic response were human recombinant platelet derived growth factor-AB heterodimer (PDGF-AB); human recombinant platelet derived growth factor-AA homodimer (PDGF-AA); human recombinant platelet derived growth factor-BB homodimer (PDGF-BB); human recombinant acidic fibroblast growth factor (aFGF); human recombinant epidermal growth factor (EGF); human recombinant insulin-like growth factor I (IGF-I); human recombinant insulin-like growth factor II (IGF-II); human recombinant transforming growth factor beta, type I (TGF-BI); human recombinant interleukin 1-beta (IL-1B); recombinant murine leukemia inhibitory factor (LIF); recombinant murine tumor necrosis factor alpha (TNF-a). Recombinant basic fibroblast growth factor (BFGF) did not elicit a mitogenic response.

OSR-2 cells respond mitogenically to a mixture of bone morphogenic proteins (BMP-2, BMP-3, BMP-4, and BMP-7) as isolated from bovine bone by Koenig et al., (1991) *J. Bone Mineral Res.*, Vol. 6, pp. S206. The BMPs have been shown to induce the formation of cartilage and bone in vivo (reviewed by Wozney (1989) "Progress in Growth Factor Research," Vol. 1, pp. 267-280).

Figure 1:
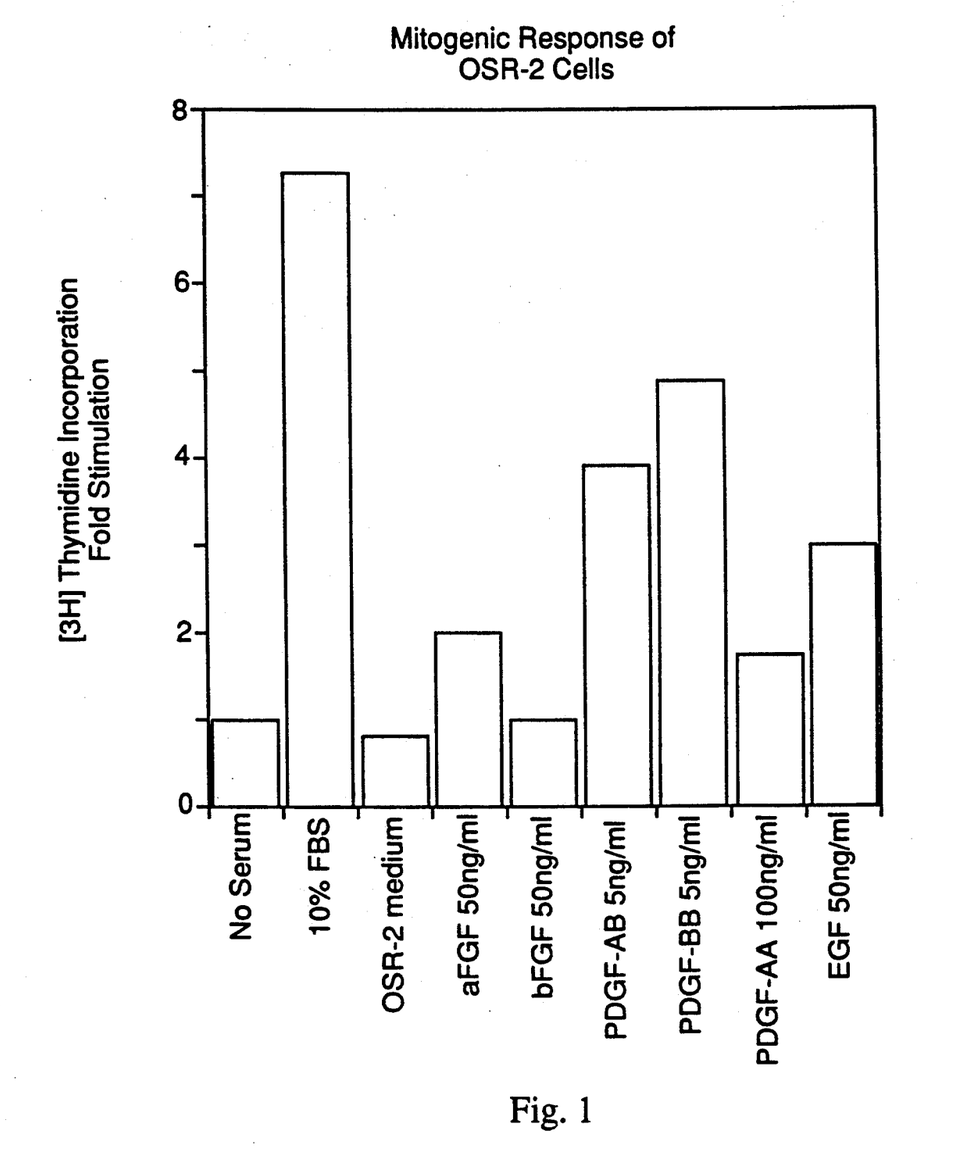
FIG. 1 shows the mitogenic response of OSR-2 to various growth factors.
Figure 2:
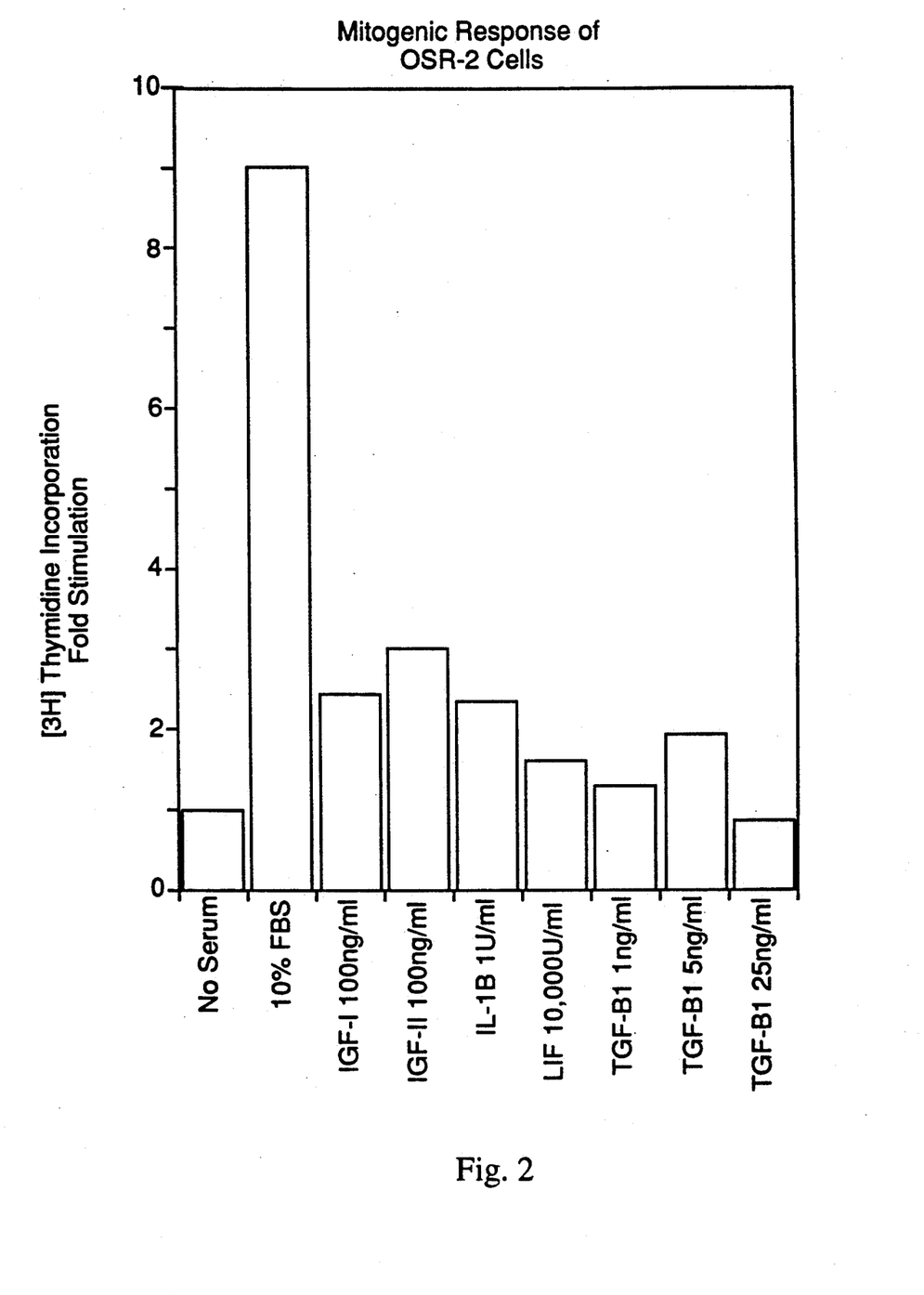
FIG. 2 also shows the mitogenic response of OSR-2 to various growth factors.

The mitogenic responses of OSR-2 cells were compared to the responses of other cell lines of mesenchymal origin. These cell lines include the osteoblastic MC3T3-E1 cells (Sudo et al., (1983) *J. Cell Biol.*, Vol. 96, pp. 191-198); the fibroblastic MRC-5 (American Type Culture Collection, CCL p. 171); the fibroblastic NIH-3T3 (American Type Culture Collection, CRL 1658); the multipotential cell line, C3H10T1/2, clone 8 (American Type Culture Collection, CCL 226); the multipotential cell population isolated from neonatal rat muscle (designated NRM) according to slight modifications of the procedure describe by Sampath et al., (1984) *Proc. Natl. Acad. Sci. USA*, Vol. 81, pp. 3419-3423. Briefly, the tricep muscles were aseptically isolated from euthanized newborn Sprague-Dawley rats and cleaned of connective and vascular tissue. The muscles were minced and cultured in 15 ml of 10% fetal bovine serum, 90% CMRL-1066 medium (GIBCO) supplemented with antibiotics and antimycotic mixture (penicillin, 100 units/ml; streptomycin, 100 ug/ml; Fungizone, 0.25 ug/ml, GIBCO). Once the explant cultures reached confluence in a 150 cm$^2$ tissue culture flask, the NRM cell line was designated as being at mean population doubling of 1. The NRM cell line is capable of forming multinucleate myotubes in confluent cultures and can be stimulated by TGF-B1 to differentiate into chondrocyte-like cells (Seyedin et al., (1985) *Proc. Natl. Acad. Sci. USA*, Vol. 82, pp. 2267-2271). The mitogenic responses of the above mentioned cell lines to various growth factors and comparison to the responses of the OSR-2 cell line are shown in FIG. 1 and 2, and are summarized in Table 2.

In addition to responding mitogenically to a number of growth factors, the OSR-2 cell line has an advantage over the other target cell lines tested in that the cells do not produce detectable autocrine growth factors which could possibly compromise the interpretation of mitogenicity assays of other factors. This was established by culturing confluent cells for 24 hours in the presence of serum-free growth medium. This serum-free conditioned medium was clarified by centrifugation and used in the [$^3$H]thymidine incorporation assay to test for mitogenic factors. The results of this analysis indicated that OSR-2 does not produce autocrine growth factors, nor does the conditioned medium stimulate a mitogenic response in the MC3T3-E1, MRC-5, NRM, and C3H10T1/2 cell lines. However, serum-free conditioned medium from MC3T3-E1 was mitogenic for MC3T3-E1 cells; serum-free conditioned medium from MRC-5 was mitogenic for MRC-5 cells; and serum-free medium from MRC-5 was mitogenic for MRC-5 cells; and serum-free conditioned medium from C3H10T1/2 was mitogenic for C3H10T1/2 cells. The results indicate that MC3T3-E1, MRC-5, and C3H10T1/2 cells are capable of secreting autocrine growth factors. No mitogenic activity was observed in the conditioned serum-free from NRM cells, suggesting that these cells, like the OSR-2 cells, do not secrete autocrine growth factors.

TABLE 2

| Proteins | ATCC No. 11065 | MC3T3-E1 | NRM | C3H10T½ | MRC-5 | NIH3T3 |
|---|---|---|---|---|---|---|
| 0% Serum control | 0 | 0 | 0 | 0 | 0 | 0 |
| 10% Serum | + | + | + | + | + | + |
| PDGF-AA | + | + | + | + | + | ND |
| PDGF-AB | + | + | + | + | + | + |
| PDGF-BB | + | + | + | + | + | ND |
| EGF | + | + | + | + | + | + |
| aFGF | + | + | + | + | + | + |
| bFGF | 0 | + | 0 | + | 0 | 0 |
| IGF-I | + | + | + | + | + | + |
| IGF-II | + | + | + | + | + | + |
| TGF-B1 | + | − | 0 | + | 0 | + |
| IL-IB | + | + | + | + | ND | + |
| LIF | + | 0 | + | 0 | ND | 0 |
| TNF-a | + | + | + | ND | ND | + |
| BMP-2, 4, 6, 7 | + | − | 0 | + | + | + |
| ATCC No. 11065 | 0 | 0 | 0 | 0 | 0 | ND |

0 = no stimulation (equivalent to 0% serum control), + = mitogenic stimulation at least 50% above the 0% serum control, − = inhibition of proliferation at least 50% of 0% serum control.

Use of the OSR-2 Cell Line as an Indicator Cell For Differentiation Factors

The proper development, maintenance, and repair of tissues requires a balance between positive regulators and negative regulators of cellular proliferation. Growth factors have been demonstrated to act as positive and negative regulators of cellular proliferation and to influence the differentiation of cells (Aaronson (1991) *Science*, Vol. 254, pp. 1146–1153; Cross and Dexter (1991) *Cell*, Vol. 64, pp. 271–280; Wang and Hsu (1986) *Trends Biochem. Sci.*, Vol. 11, pp. 24–26). One of the characteristics of a fully differentiated cell is that the cell is postmitotic and is no longer proliferating. Thus, the ability to negatively regulate cellular proliferation is a feature of some growth factors which influence differentiation. The OSR-2 cell line, in addition to being useful as an indicator of mitogenic growth factors, also has utility as an indicator cell for differentiation factors which influence mesenchymal cells in general and cells of the osteoblast lineage in particular. The ability of OSR-2 cells to respond to a differentiation factor can be assayed by measuring a decrease in cellular proliferation relative to cells not treated with the differentiation factor, in a manner similar to that used to measure an increase in cellular proliferation in response to mitogenic growth factors.

The invention has been described herein with reference to certain preferred embodiments and examples. Obvious variations may appear to those skilled in the art. Therefore, the invention is not to be considered limited thereto but only by the claims which follow.

What is claimed is:

1. A cell line having all of the identifying characteristics of American Type Culture Collection Accession No. CRL 11065.

* * * * *

UNITED STATES PATENT AND TRADEMARK OFFICE
CERTIFICATE OF CORRECTION

PATENT NO. : 5,286,644

DATED : February 15, 1994

INVENTOR(S) : Doersen et al.

It is certified that error appears in the above-indentified patent and that said Letters Patent is hereby corrected as shown below:

Column 2, line 61, "tunorigenic" should read --tumorigenic--.

Column 11, line 59, "type I" should read --type 1--.

Column 11, line 59, "TGF-BI" should read --TGF-B1--.

Column 13, line 15 of Table 2, "IL-IB" should read --IL-1B--.

Signed and Sealed this

Twenty-first Day of March, 1995

Attest:

BRUCE LEHMAN

Attesting Officer

Commissioner of Patents and Trademarks